United States Patent [19]

Allen

[11] Patent Number: 4,808,521

[45] Date of Patent: Feb. 28, 1989

[54] DOUBLE-LABELED ENZYMEIMMUNOASSAY METHODS

[75] Inventor: Gerald J. Allen, Windlesham, England

[73] Assignee: Serone Diagnostics Partners, Braintree, Mass.

[21] Appl. No.: 821,428

[22] Filed: Jan. 22, 1986

[30] Foreign Application Priority Data

Jan. 23, 1985 [GB] United Kingdom ............... 8501671

[51] Int. Cl.$^4$ ............... G01N 33/53; G01N 33/543; G01N 33/566; C12Q 1/00

[52] U.S. Cl. ............................ 435/7; 435/4; 435/810; 436/501; 436/518

[58] Field of Search .............. 435/7; 436/518, 526

[56] References Cited

U.S. PATENT DOCUMENTS

| 4,540,659 | 9/1985 | Litman et al. ..................... 435/7 |
| 4,659,678 | 4/1987 | Forrest et al. ..................... 436/513 |

FOREIGN PATENT DOCUMENTS 0075379 3/1983 European Pat. Off. .
0105714 4/1984 European Pat. Off. .
1292556 12/1986 Japan .
WO8002076 10/1980 World Int. Prop. O. .

*Primary Examiner*—Robert J. Warden
*Assistant Examiner*—Janelle Graeter
*Attorney, Agent, or Firm*—Ostrolenk, Faber, Gerb & Soffen

[57] ABSTRACT

The present invention provides a method of performing an immunoassay of a ligand in a liquid sample wherein two independently measureable enzyme labels are separately conjugated to two or more components or populations of components of the assay system and, after completion of the complexing reaction, substantially all of the first enzyme label and a proportion of the second enzyme label are removed from the assay mixture, the proportion of the second label removed being related to the amount of the said ligand and the assay determined from a measurement of said proportion of the second label being normalised by comparison with a measurement of the total first label removed.

In this way, manual pipetting errors and other assay procedural errors can be corrected for.

17 Claims, No Drawings

DOUBLE-LABELED ENZYMEIMMUNOASSAY METHODS

The present invention relates to methods of immunoassay of antigens and to kits for carrying out such methods. In particular, it relates to improvements in immunoassays which employ enzyme-labelled antibodies to quantify the antigen under assay (hereinafter referred to as enzyme immunoassays).

Enzyme immunometric assays may be classified into various types, for example 1-site and 2-site assays, according to the techniques employed. In a conventional 1-site enzyme immunoassay, the antigen under assay (hereinafter referred to as "ligand") competes with a ligand analogue (i.e. a reagent having the same complexing characteristics as the ligand, the term "ligand analogue" including within its scope a known quantity of the ligand under assay) for enzyme-labelled antibody and, after completion of the complexing reaction, ligand analogue with bound labelled antibody is separated from the assay mixture. The quantity of ligand analogue which binds with the labelled antibody will be inversely proportional to the amount of ligand present in the sample. Commonly, the ligand analogue is immobilised on a solid support to facilitate the separation step. Following separation of the solid support (together with the ligand analogue and a proportion of the labelled component) from the assay mixture after the complexing reaction has occurred, the proportion of the labelled component which has become complexed to the ligand analogue is determined and the amount of the ligand thereby calculated.

In an improved 1-site enzyme immunoassay of the type disclosed in European application No. 85306272.7, the ligand analogue is not bound directly to the solid support. Instead, the ligand analogue is conjugated with a reagent X, e.g. a hapten such as fluorescein isothiocyanate (FITC), and the solid phase has conjugated to it a binding partner specific for reagent X. Such a 1-site assay is hereinafter referred to as a 1-site enzyme immunoassay of the indirect-link type.

1-site methods may be used to assay ligands having one or more than one epitope (i.e. immunological binding site). However, where the ligand has more than one epitope, only one such site will be used in the assay.

In a conventional 2-site enzyme immunoassay, commonly referred to as a sandwich immunoassay, the ligand, which must have two or more epitopes, is insolubilised by reaction with an unlabelled antibody conjugated to a solid phase and reacted with an enzyme-labelled antibody directed to a different (preferably roomly-spaced) epitope of the ligand. The quantity of labelled antibody which becomes immobilised due to the complexing reaction is directly proportional to the amount of ligand present in the sample.

2-site enzyme immunoassays of the indirect-link type, analogous to the radioimmunometric assays described in our co-pending European published application no. 105714, employ two soluble antibody reagents directed to different epitopes of the ligand, one soluble antibody reagent comprising enzyme-labelled antibody molecules. The solid phase employed is conjugated to a further reagent which is capable of specifically non-covalently binding the non-labelled antibodies. These antibodies may, for example, conveniently be conjugated to a reagent X. The separation step is then achieved by using a solid phase conjugated to a specific binding partner for reagent X.

The term "antigen" as used herein will be understood to include both permanently antigenic species (for example, proteins, peptide hormones, bacteria, bacteria fragments, cells, cell fragments and viruses) and haptens which may be rendered antigenic under suitable conditions (including, for example, narcotics, hypnotics, analgesics, cardiovascular drugs, vitamins, non-peptide hormones and metabolites thereof, antibiotics, pesticides and sugars.).

The term "antibody" as used herein includes within its scope:

(a) any of the various classes or sub-classes of immunoglobulin, e.g. IgG, IgM, derived from any of the animals conventionally used, e.g. sheep, rabbits, goats or mice;

(b) monoclonal antibodies; and (c) fragments of antibodies, monoclonal or polyclonal, the fragments being those which contain the binding region of the antibody, i.e. fragments devoid of the Fc portion (e.g., Fab, Fab', F(ab')$_2$) or the so-called "half-molecule" fragments obtained by reductive cleavage of the disulphide bonds connecting the heavy chain components in the intact antibody.

The methods for preparation of antigen-binding fragments of antibodies are well-known in the art and will not be described herein. The techniques for preparing monoclonal antibodies are also well-known (see, for example Galfre G. & Milstein C. (1981). "Preparation of Monoclonal Antibodies: Strategies and Procedures" in Methods in Enzymology 73, 1–46).

In particular, the following antigens may be assayed by 1-site or 2-site methods as hereinbefore described: hormones, including peptide hormones (e.g. thyroid stimulating hormone (TSH), luteinising hormone (LH), follicle stimulating hormone (FSH), human chorionic gonadotrophin (hCG), insulin and prolactin), and non-peptide hormones (e.g. steroid and thyroid hormones), proteins (e.g. carcinoembryonic antigen (CEA) and alphafetoprotein (AFP)), drugs, sugars, toxins and vitamins.

Such assay methods are, however, very susceptible to variations in the physical conditions under which they are performed, particularly variations arising from deviations from the defined assay procedure. The main sources of imprecision in immunoassays are associated with factors such as poor pipetting which gives rise to wrong reagent volumes being added, poor timing which means that some assay tubes can have differing reaction times with the reagents and poor tube manipulation where a separation stage is needed (e.g. by centrifugation or magnetic separation followed by decantation or aspiration). While assay procedural errors are more likely to occur with a manual operator, automated instruments for performing immunoassays are not infallible and can, for example, on occasions deliver imprecise reagent volumes or give rise to variable reaction times.

We have now devised improved enzyme immunoassays wherein variations associated with random or systematic operator errors can be compensated for i.e. internal normalisation can be achieved, as a result of use of a second enzyme label.

Immunoassays employing two labels (e.g. two fluorescent labels), one for quantification of the antigen under assay and one for increasing precision, have previously been disclosed in published PCT application No. WO 80/02076. However, this published application which concerns overcoming sources of inaccuracy in immunoassays, particularly in fluorescent immunoassays, other than random or systematic operator errors (e.g. in a 2-site or competitive assay employing a solid phase, signal variation not as a result of the quantity of label being detected, but as a result of physical variation in the nature of the presentation of the label) does not disclose the use of two enzyme labels. Indeed, it is stated that where a receptor ligand which binds immunologically to the sample ligand is to be detected by means of a conjugated label for quality control or for instrument calibration prior to incubation, it may be impractical to tag the receptor ligand with an enzyme.

However, we have found that it is, in fact, possible to use two enzyme labels in immunoassay systems and that this has the advantage of avoiding the use of radioactive and/or fluorescent labels, both of which have disadvantages. Radioactive labels require special handling techniques and may be unsuitable for use by unskilled operators. Fluorescent labels usually require the use of fluorimeters capable of working with ultraviolet radiation, which are relatively expensive for routine use. Enzymes, on the other hand, can be used with substrates generating coloured solutions capable of being assayed using colorimeters, which are much simpler and generally less expensive than fluorimeters. Furthermore, whereas very low levels of fluorescent labels are difficult to estimate, low levels of enzyme labels can be estimated by simply increasing the time of the assay as one molecule of enzyme can produce many molecules of product, thus giving a high gain and amplifying the colour reaction. Enzyme systems are less susceptible to background interference than fluorescent systems and the use of fluorescent labels has the additional disadvantage that fluorescent compounds tend to be unstable in light.

In one aspect, the present invention provides a method of performing an immunoassay of a ligand in a liquid sample, wherein two independently measurable enzyme labels are separately conjugated to two or more components or populations of components of the assay system and, after completion of the complexing reaction, substantially all of the first enzyme label and a proportion of the second enzyme label are removed from the assay mixture, the proportion of the second label removed being related to the amount of the said ligand and the assay determined from a measurement of said proportion of the second label being normalised by comparison with a measurement of the total first label removed.

The separation step may, for example, be achieved by the component(s) conjugated to the first label being directly or indirectly-linked to a solid support. The solid support may, for example, be in the form of finely divided inert particles or beads (e.g. latex particles) and such particles or beads may if desired be magnetic or magnetisable to facilitate the separation step. Suitable magnetic or magnetisable solid supports are described in "Immunoassays for Clinical Chemistry" (Ed. Hunter and Corrie, Churchill Livingstone, Edinburgh (1983) pp. 147-162); for example, particles of cellulose composite containing $Fe_3O_4$ may be used.

In order to use a second enzyme label for internal normalisation of all stages of an enzyme immunoassay, including the final enzyme reaction step, where imprecision can arise from errors in pipetting, timing, temperature etc., it is necessary to use two suitable enzymes which can be assayed simultaneously, so that the same potential variations and errors are applied to both reactions. It is thus necessary to identify two suitable enzyme-substrate pairs which not only fulfil the criteria necessary for enzyme immunoassays (ability of the enzymes to be conjugated to an appropriate component with little or no loss of enzyme or immunological activity, and freedom from interference by the sample or assay conditions) but which, under certain conditions, do not interact with one another during the immunoreaction and can simultaneously catalyse separate substrate conversions to generate products which can be measured independently of one another.

We have found requirements for substrate conversions by the two enzymes alkaline phosphatase and $\beta$-galactosidase that are essentially compatible so that these two enzymes can be assayed simultaneously.

The method of the present invention is applicable, for example to both 1-site and 2-site enzyme immunoassays.

Thus, according to one embodiment of the invention, we provide a method of performing a 1-site enzyme immunoassay of a ligand with one or more epitopes in a liquid sample, which includes the steps of (a) incubating the sample sequentially or simultaneously with a ligand analogue labelled with a first enzyme label and with an antibody to the ligand labelled with a second enzyme label (such that the said first enzyme label may be monitored independently of the said second enzyme label) to achieve complexing;

(b) separating the complexed components containing the said first enzyme label from the fraction of said second enzyme label uncomplexed with ligand analogue; and (c) determining a normalised assay of the ligand by measuring the amount of the said second enzyme label in the separated complexed components from step (b) containing said first enzyme label with respect to a measurement of the said first enzyme label present in the said separated components.

This feature of the invention is applicable to all 1-site enzyme immunoassays. In particular, however, it may be applied to 1-site enzyme immunoassays of the indirect-link type described in our copending European Patent Application No. 85306272.7 to give internally normalised versions of such assays.

Thus, in a preferred feature of the present invention, we provide a method of performing a 1-site immunoassay according to the present invention wherein the ligand analogue labelled with the first enzyme label is also tagged with a reagent X (the said reagent not being present as a free reagent in the assay mixture) and step (b) is accomplished by means of a solid phase carrying a binding partner specific for reagent X.

The reagent X may conveniently be a hapten, for example, selected from fluorescein derivatives (e.g. fluorescein isothiocyanate (FITC)), rhodamine isothiocyanate, 2,4-dinitrofluorobenzene, phenyl isothiocyanate and dansyl chloride and the specific binding partner for reagent X in this case will be an antibody thereto. Preferred as reagent X are derivatives of fluorsecein, particularly FITC. When reagent X is FITC, the binding partner specific therefor on the solid phase may be anti-FITC antibody covalently linked to the solid support. The antiserum may be prepared in conventional manner, for example by immunising sheep with FITC conjugated to keyhole limpet haemocyanin. Coupling of the antiserum to the solid support may, for example, be effected using the method of Axen et al (Nature 214, 1302-1304 (1967)). An alternative convenient binding system to the reagent X/-anti-reagent X system described above is an avidin/biotin binding system.

According to a second embodiment of the invention, we provide a method of performing a 2-site enzyme immunoassay of a ligand with more than one epitope in a liquid sample, which includes the steps of (a) incubating the sample in the presence of a reagent comprising two or more populations of antibodies to the ligand which can complex simultaneously with the ligand (the reagent employing two enzyme labels such that a first label in one of the populations may be monitored independently of a second label in the other population(s)), to achieve complexing equilibrium;

(b) separating the components containing said first enzyme label from those containing uncomplexed said second enzyme label; and (c) determining a normalised assay of the ligand by measuring the amount of the said second enzyme label in the separated complexed components from step (b) containing said first enzyme label with respect to a measurement of the said first label present in the said separated components.

It will be appreciated that the components containing the first enzyme label, separated according to step (b) from those containing uncomplexed second enzyme label, will also contain the complexed fraction of the second enzyme label. Thus, step (b) simultaneously also effects separation of complexed and uncomplexed phases of the reagent carrying the second label.

This feature of the invention is applicable to all 2-site enzyme immunoassays. In particular, however, it may be applied to sandwich enzyme immunoassays of the indirect-link type to give internally normalised versions of such assays.

Thus, in a preferred feature of the present invention, we provide a method of performing a 2-site immunoassay according to the present invention which comprises incubating a mixture of:

(a) the liquid sample;

(b) a reagent comprising antibodies to the ligand labelled with a first enzyme label;

(c) a reagent comprising antibodies to the ligand labelled with a second independently measureable enzyme label; and (d) a reagent capable of binding to component (b) by non-covalent bonding, but which is not directly bindable to either component (a) or component (c), the said reagent (d) being bound to a solid phase support;

separating the solid phase from the assay mixture and determining a normalised assay of the ligand by measuring the amount of the said second enzyme label in the separated solid phase components with respect to a measurement of the said first label present in the said separated components.

It is particularly preferred for component (b) to comprise antibodies conjugated to a reagent X in addition to the first enzyme label and for reagent (d) to be a specific binding partner for reagent X (the said reagent not being present as a free reagent in the assay mixture). Suitable reagent X/specific binding partner pairs are as hereinbefore described for 1-site enzyme immunoassays.

Preferably, the two enzyme labels employed in a method of immunoassay according to the present invention are capable of simultaneously converting substrates to independently measureable products and, following the separation step, the amounts of the two labels removed from the assay mixture are determined by means of concurrent enzyme reactions. Desirably, the products of the two concurrent enzyme reactions are independently measurable by absorbance measurements.

Two suitable enzyme-substrate pairs for use together in a method of immunoassay according to the present invention are alkaline phosphatase/phenolphthalein monophosphate and $\beta$-galactosidase/p-nitrophenyl-$\beta$-D-galactoside (p-NPBG). If desired, p-nitrophenyl-$\beta$-D-galactoside can be replaced by o-nitrophenyl-$\beta$-D-galactoside. Alkaline phosphatase and $\beta$-galactosidase are currently particularly preferred for use as labels in conventional enzyme immunoassays, primarily because they can be readily linked to other proteins (e.g. antibodies) without substantial loss of activity [see, for example, Ishikawa et al. in J. Immunoassay 4, 209-327 (1983) and Annals of Clinical Biochemistry 21 (1984) p. 434-443] and catalyse reactions which give rise to coloured products.

The optimum pH for hydrolysis of phenolphthalein monophosphate by alkaline phosphatase is 9.8. We have found that in the presence of a high concentration (about 0.25 M to 1 M) of diethanolamine the pH can be reduced to 8.6 with no loss of activity.

$\beta$-galactosidase has a pH optimum of 7.4 for p-nitrophenyl-$\beta$-D-galactoside (p-NPBG), although in a single assay format using normal substrate concentrations (up to approximately 5mM), the pH can be raised to 8.6 with only a slight loss (approximately 20%) of activity. However, in the same assay system, but containing about 1M diethanolamine, the activity of $\beta$-galactosidase is almost totally abolished. The kinetics of inhibition of $\beta$-galactosidase by diethanolamine are complex, but the major effect is a competitive one with the Km of $\beta$-galactosidase for p-NPBG in the presence of 1M diethanolamine being altered from 66 $\mu$M to 21 mM. We have found that by increasing the concentration of p-NPBG at pH 8.6, even in the presence of about 1M diethanolamine, substantial activity of $\beta$-galactosidase can be achieved.

Thus, if the chosen enzyme labels for a method of immunoassay according to the present invention are alkaline phosphatase and $\beta$-galactosidase, the amounts of the two labels removed from the assay mixture in the separation step may, for example, be determined by incubation in the presence of a substrate buffer solution at pH 8.6 initially comprising about 0.25 M to 1 M diethanolamine, about 10 mM phenolphthalein monophosphate and about 50 mM p-nitro-phenyl-$\beta$-D-galactoside. The conversion of phenolphthalein monophosphate to phenolphthalein by the alkaline phosphatase label is preferably monitored by measurement of absorbance at 554 nm, while the simultaneous conversion of p-NPBG to p-nitrophenol by the $\beta$-galactosidase label is preferably monitored by measurement of absorbance at 404 nm, a correction being made for the low absorbance of phenolphthalein at this wavelength.

The immunoassays of the present invention have the advantage that high consistent accuracy can be achieved without the need for complex instrumentation. No special safety precautions are required as in the case of immunoassays employing radioisotope labels, nor is background interference a problem as with fluorescent immunoassays.

In a further feature of the present invention, we provide kits of reagents for carrying out a method of immunoassay according to the invention. Such a kit may, for example, comprise a first component labelled with an enzyme label and a second component labelled with a different, distinguishable, enzyme label. Thus, in the case of a kit for a 1-site immunoassay according to the present invention, said first component will comprise an enzyme-labelled ligand analogue and said second component will comprise antibodies to the ligand labelled with a second enzyme label. The said first component may be conjugated to a solid support. Alternatively, in the case of a kit for a 1-site immunoassay according to the present invention of the indirect-link type, said first component will be conjugated to a reagent X, in addition to an enzyme label, and the kit may further comprise a solid support conjugated to a specific binding partner for reagent X.

A kit of reagents for a 2-site immunoassay according to the present invention may comprise a first population of antibodies to the ligand labelled with an enzyme label and a second population of antibodies to the ligand labelled with a different enzyme label, said populations of antibodies being directed to two different epitopes. The said first population of antibodies may be conjugated to a solid support or the kit may further comprise a separate solid support. Thus, for example, if said first population of antibodies is conjugated with a reagent X, in addition to the enzyme label, for use in a 2-site immunoassay according to the invention of the indirect-link type, the kit may further comprise a solid support conjugated to a specific binding partner for reagent X.

For convenience of use, two or more components of a kit according to the present invention may be combined in a single reagent. One or more compnents may be supplied in lyophilized form.

As stated above, the method of the present invention enables internally normalised assays to be carried out. Without wishing to be bound by theoretical considerations, we believe that in the case of an immunoassay according to the invention employing a solid support, the signal from the first label, after separation of the phases, will be independent of the concentration of ligand but will be dependent on the coupling reaction with the solid phase (in particular on the volume and concentration of the solid phase and the time and temperature of incubation), the efficiency of the phase separation and variations in the physical conditions under which the label is monitored (e.g. incubation time, temperature, etc.), whereas the signal from the second label, after separation, will be dependent on the concentration of ligand in the sample, the coupling reaction with the solid phase, the efficiency of the phase separation and variations in the physical conditions under which the label is monitored. Thus by normalising the signal from label 2 with that from label 1, the effect of variations in many of the parameters affecting the assay can be controlled and the dose-response relationship stabilised.

The following non-limiting Examples are intended to illustrate the present invention.

EXAMPLE 1

Correction of substrate incubation volume and incubation time in an assay for luteinising hormone (LH)

Preparation of Starting Materials

1. Preparation of anti-LH antibodies

Monoclonal antibodies were obtained from mouse ascites fluid by the process reported by Milstein and Kohler in *Nature* 256 (1975) p. 495-497. Antibodies from individual hybridoma cell lines were screened to identify those producing antibody to discrete antigenic determinants. Those having the highest affinities to LH were selected for use in the assay.

2. Preparation of alkaline phosphatase/anti-LH conjugate 0.16 ml N-succinimidyl 4-(N-maleimidomethyl) cyclohexane-1-carboxylate (SMCC) (60 mM in dimethylformamide-DMF) was added to 1.6 ml of alkaline phosphatase (2 mg/ml in 50 mM sodium borate, 1 mM magnesium chloride and 0.1 mM zinc chloride, pH 7.6) and incubated for 1 hour at 30° C. The enzyme was separated by passage through a Sephadex G-25 medium column (1×35 cm) equilibrated in 0.1 M Tris, 1 mM magnesium chloride and 0.1 mM zinc chloride, pH 7.0. The purified enzyme was stored at +4° C. until required.

16.3 μl of N-succinimidyl 3-(2-pyridyldithio) propionate (SPDP) (25 mM in ethanol) were added to 1 ml of anti-LH monoclonal antibody (3 mg/ml in 200 mM sodium propionate, pH 6.0) and incubated for 30 minutes at room temperature. The antibody was separated by passage through a disposable Sephadex G-25 column (PD-10) equilibrated in 200 mM sodium acetate buffer, pH 4.5. Dithiothreitol (1 M) was added to the antibody (1/20 of antibody volume added) and left for 10 minutes at room temperature. The antibody was desalted using a Sephadex G-25 medium column (1×35 cm) equilibrated in 200 mM sodium propionate, pH 6.0.

Antibody and alkaline phosphatase prepared as above were mixed in an equimolar ratio and left to conjugate for 24 hours at 4° C. The resulting conjugate was purified by high-performance liquid chromatography (HPLC) on a TSK 3000 SW column equilibrated in 200 mM sodium propionate, 1 mM magnesium chloride and 0.1 mM zinc chloride at pH 6.0. The conjugate was diluted in assay buffer to a concentration of 2.5 μg/ml for use in the assay.

3. Preparation of anti-LH, conjugated to β-galactosidase and fluorescein isothiocyanate (FITC)

2.5 mg of anti-LH, specific for a different epitope on the LH molecule than the antibody conjugated to alkaline phosphatase, was dissolved in bicarbonate buffer (0.02 M, pH 9.1) and mixed with 500 ul of 0.5 mg/ml FITC. After an overnight incubation at 4° C., conjugate was purified by passage down a Sephadex G-25 column equilibrated with sodium propionate buffer (0.2 M, pH 6.0).

150 μl of SPDP (25 mM in ethanol) was added to the purified conjugate and incubated for 30 minutes at room temperature. A further purification step was then undertaken by HPLC on a TSK 300 SW column again equilibrated with sodium propionate (0.2 M, pH 6.0). The conjugate was then mixed with an equimolar concentration of β-galactosidase, also in sodium propionate buffer (0.2 M, pH 6.0) and incubated overnight at 4° C. The resulting conjugate was purified on a TSK 4000 column equilibrated with sodium propionate buffer (0.2 M, pH 6.0). The conjugate was diluted to a concentration of 7.7 μg/ml in assay buffer for use.

4. Preparation of anti-FITC antibody covalently coupled to magnetisable solid phase Anti-FITC was a conventional polyclonal antiserum obtained by immunising sheep with FITC conjugated to keyhole limpet haemocyanin. The magnetisable cellulose particles were a composite of cellulose containing approximately 50% black ferric(ous) oxide ($Fe_3O_4$), with mean particle diameter of 3 microns (see Forrest and Rattle, "Magnetic Particle Radioimmunoassay" in Immunoassays for Clinical Chemistry, p. 147-162, Ed Hunter and Corrie, Churchill Livingstone, Edinburgh (1983)). Anti-FITC antiserum was covalently coupled to the magnetisable cellulose following cyanogen bromide activation of the cellulose, according to the procedure of Axen et al., Nature 214, 1302-1304 (1967). The antiserum was coupled at a ratio of 2 ml antiserum to 1 gram of magnetisable solid phase.

The solid phase was diluted to 2.5 mg/ml in 50 mM Tris/HCl buffer, pH 8.0, containing 0.1% sodium azide, 0.5% bovine serum albumin (BSA), fraction V, 0.25% Tween 20 and 0.5% methocell.

5. Preparation of LH standard solutions

A preparation of freeze dried LH, calibrated against International Reference Preparation 68/40, was diluted in bovine serum to give concentrations of 0, 1, 2, 10, 25, 50, 100 and 200 mIU/ml.

6. Preparation of the assay buffer

The assay buffer consisted of 0.5% BSA, fraction V, 0.2% sheep serum, 1 mM magnesium chloride, 0.1 mM zinc chloride, 0.1 M sodium chloride and 0.2% sodium azide in 0.1 M Tris/HCl, pH 8.0.

7. Preparation of the wash buffer

The wash buffer consisted of 0.9% sodium chloride in 0.01 M Tris/HCl, pH 8.6.

8. Preparation of the substrate buffer

The substrate buffer consisted of a 0.25 M solution of diethanolamine containing 0.9% sodium chloride and 1 mM magnesium chloride at pH 8.6. This buffer then had the substrate for alkaline phosphatase (10 mM phenolphthalein monophosphate) and for $\beta$-galactosidase (50 mM p-nitrophenol-$\beta$-D-galactoside) dissolved in it.

9. Preparation of the stop solution

The stop solution was prepared by adjusting a solution comprising 50mM sodium carbonate, 5mM sodium phosphate and 50mM sodium EDTA to pH 12 and then adding 25mM NaOH.

Assay Methodology

100 $\mu$l of each standard was pipetted, in duplicate, into polystyrene assay tubes. 50 $\mu$l of each antibody-enzyme conjugate and 100 $\mu$l of assay buffer were added to each tube. All tubes were mixed and incubated for 20 minutes at 37° C. 200 $\mu$l of magnetisable anti-FITC solid phase was added to each tube followed by mixing and incubation for 5 min at 37° C. The solid phase was separated magnetically, the supernatant being decanted and 500 $\mu$l of wash buffer added to each tube. After mixing, the solid phase was again separated magnetically. This washing procedure was repeated twice more and, after the final wash, the tubes were inverted and allowed to drain for 5 min.

300 $\mu$l of substrate solution was added to each tube, mixed and the tubes incubated for 15 min at 37° C. 1 ml of stop solution was added to each tube and the assay separated magnetically. The absorbances of the supernatant at 404 nm and 554 nm were determined on a Hewlett Packard (HP 8451A Diode Array) spectrophotometer, the product of the $\beta$-galactosidase reaction absorbing at 404 nm and the product of the alkaline phosphatase reaction absorbing at 554 nm. The alkaline phosphatase reaction product also absorbs slightly at 404 nm and therefore the absorbances at 404 nm were corrected accordingly.

The alkaline phosphatase activity correlates positively with the concentration of LH and thus a standard curve can be constructed from the absorbance values at 554 nm. $\beta$-galactosidase activity, the internal calibrator, should remain constant throughout the standard curve.

Ten standard curves were prepared and the mean optical density (O.D.) at 554 nm calculated for each standard. The overall mean O.D. at 404 nm was also calculated. Thus the expected absorbances for standard and calibrator were defined.

Variations in assay conditions influence the observed absorbances at both 404 and 554 nm. Absorbances at 554 nm are normalised using the following expression:

$$\text{Normalised } O.D._{554} = \text{Observed } O.D._{554} \times \frac{\text{Expected } O.D._{404}}{\text{Observed } O.D._{404}}$$

Normalised absorbances at 554 nm should fall within ±15% of the expected mean for that standard.

Experiments to test the internal normalisation of the LH assay

The first series of experiments involved the alteration of the substrate volume present at the enzyme incubation step in the assay, both decreasing the amount (250 $\mu$l) and increasing it (350 $\mu$l). The results (Table 1) show that at high concentrations of LH, altered substrate volumes result in the assay showing an error greater than the 15% of the expected values. After applying the internal normalisation correction factor, the LH values once again are within ±15% error of the expected values. Thus, the internal normalisation can correct for error in substrate volume.

The length of the substrate incubation period was then varied, increasing it to 20 minutes and decreasing it to 10 minutes. In both cases, applying the internal normalisation procedure to the observed data corrected the LH concentration values to within ±15% of the expected value (Table 2). This shows that the internal normalisation procedure can correct for wrong substrate incubation times.

EXAMPLE 2

Correction of substrate incubation volume and incubation time in an assay for thyroxine (T4)

Preparation of starting materials

1. Preparation of anti-T4 antibodies

The method was the same as used to prepare the anti-LH antibodies used in Example 1.

2. Preparation of alkaline phosphatase/T4/FITC conjugate

Alkaline phosphatase was coupled to thyroxine by the method of Erik, Washington and Laing, Annals of Clinical Biochemistry 21 (1984) p. 434-443. 37.5 nmol of enzyme in 3 ml of bicarbonate buffer (0.02 M, pH 9.1) were added to 12 ml of 0.04 M barbitone buffer pH 9.4. To this solution was added 3.75 $\mu$mol thyroxine in 2.5 ml 0.01 M sodium hydroxide followed by 2.5 umol glutaraldehyde in 50 $\mu$l of water. After 2½ hours at 23° C., 20 $\mu$mol of L-lysine hydrochloride solution in 200 $\mu$l of water were added followed 1 hour later by the addition of 3.75 $\mu$mol sodium borohydride in water and further incubation at 0° C. for 1 hour. After dialysis of the product for 48 hours at +4° C., the sample was concentrated by ultrafiltration on an Amicon YM10 membrane and subjected to successive chromatography on a Sephadex G-25 column equilibrated with triethanolamine buffer (0.1 M, pH 7.0) three times. The material was then purified by passage down a high performance liquid chromatography column (TSK 3000 SW) eluted with triethanolamine buffer (100 mM, pH 7.0). The eluted material was equilibrated into bicarbonate buffer (0.02 M, pH 9.0) by passage down a Pharmacia G-25 PD10 column, and coupled to fluorescein isothiocyanate (FITC) at 0.083 mg per ml of conjugate by overnight incubation at 4° C. The resulting FITC/T-4/alkaline phosphatase conjugate was purified by passage down a Pharmacia PD10 G-25 column equilibrated in triethanolamine buffer (0.1 M, pH 7.0).

3. Preparation of anti-T4 antibody conjugated to β-galactosidase

150 μl of SPDP (25 mM in ethanol) was added to 9.4 ml of anti-T4 antibody at 100 μg/ml in 0.2M sodium propionate buffer at pH 6.0 and incubated at room temperature for 30 minutes. The resulting antibody was then purified by passage down an HPLC TSK 3000 SW column equilibrated in sodium propionate buffer (0.02 M, pH 6.0). The antibody thus obtained was then mixed with an equimolar concentration of β-galactosidase and incubated overnight at 4° C. before purification on a TSK 4000 column equilibrated in sodium propionate buffer (0.2 M, pH 6.0).

4. Preparation of anti-FITC antibody covalently coupled to magnetisable solid phase The method of preparation of this reagent was the same as in Example 1 except that the solid phase was diluted to a concentration of 7.5 mg/ml for use in the T4 assay.

5. Preparation of Standard solutions of T4

L-thyroxine, sodium salt (Sigma (London) Chemical Co.) was dissolved in 0.1M sodium hydroxide solution and then diluted with T4-stripped human serum to give a stock solution of 21.23 μg T4/ml. This stock solution was then further diluted with T4-stripped human serum to give final T4 concentrations of 0, 25.6, 51.1, 117, 163, 215 and 311 ng T4/ml. The zero T4 samples were further affinity purified to removed any thyroid stimulating hormone (TSH) present in the human serum.

6. Preparation of the assay, wash, substrate buffers and stop solutions

All these reagents were the same as those described in Example 1.

Assay Methodology

This was as described for LH in Example 1 with the following modifications:

100 μl of each enzyme cojugate were added and the initial incubation period was increased to 30 min.

The substrate incubation time was increased to 60 min.

Calculations

The β-galactosidase activity correlates negatively with the concentration of T4 and thus the standard is constructed from the 404 nm absorbances. Alkaline phosphatase activity was used as the internal calibrator.

Six standard curves were prepared and the mean O.D. at 404 nm calculated for each standard. The overall mean O.D. at 554 nm was also calculated.

Absorbances at 404 nm are normalised using the following expression:

$$\text{Normalised } O.D._{404} = \text{Observed } O.D._{404} \times \frac{\text{Expected } O.D._{554}}{\text{Observed } O.D._{554}}$$

Normalised absorbances at 404 nm should fall within ±15% of the expected means for that standard.

Experiments to test the internal normalisation of the T4 assay

The first series of experiments involved the alteration of the substrate volume present during the enzyme incubation step of the assay, using both greater (350 μl) and smaller (250 μl) amounts. The results (Table 3) show that at both low and high values of T4, the application of the internal normalisation procedure will correct for any errors greater than ±15% in the assay as well as reducing the error on samples whose values fall within ±15% of the expected value. Thus, the internal normalisation procedure will correct for error in substrate volume.

The length of the substrate incubation period was then varied by decreasing it to 45 minutes and increasing it to 55 minutes. Again, the results (Table 4) show that by applying the internal normalisation procedure to the assay, any datum points whose error is greater than ±15% of the expected value, can be corrected so that the values fall within the error of the expected values. This shows that the internal normalisation procedure can correct for erroneous substrate incubation times.

TABLE 1

Results obtained by varying the volume of substrate in the LH assay (obs = observed results; norm = corrected values of LH concentration after applying the internal normalisation procedure).

| Substrate Volume (μl) | standard 1 (0 mIU/ml) | | standard 2 (1 mIU/ml) | | standard 3 (2 mIU/ml) | | standard 4 (10 mIU/ml) | | standard 5 (25 mIU/ml) | | standard 6 (50 mIU/ml) | | standard 7 (100 mIU/ml) | | standard 8 (200 mIU/ml) | |
|---|---|---|---|---|---|---|---|---|---|---|---|---|---|---|---|---|
| | obs | norm | obs | norm | obs | norm | obs | norm | obs | norm | obs | norm | obs | norm | obs | norm |
| 300 | 0.015 | | 0.022 | | 0.032 | | 0.108 | | 0.242 | | 0.448 | | 0.780 | | 1.250 | |
| 250 | 0.014 | 0.013 | 0.023 | 0.022 | 0.033 | 0.031 | 0.110 | 0.105 | 0.249 | 0.239 | 0.464 | 0.445 | 0.854 | 0.819 | 1.357 | 1.301 |
| 350 | 0.011 | 0.012 | 0.017 | 0.017 | 0.026 | 0.027 | 0.092 | 0.097 | 0.213 | 0.223 | 0.393 | 0.413 | 0.651 | 0.684 | 1.092 | 1.147 |

TABLE 2

Results obtained by varying the volume of substrate incubation time in the LH assay (obs = observed results; norm = corrected values of LH concentration after applying the internal normalisation procedure).

| Substrate Incubation Time (Min) | standard 1 (0 mIU/ml) | | standard 2 (1 mIU/ml) | | standard 3 (2 mIU/ml) | | standard 4 (10 mIU/ml) | | standard 5 (25 mIU/ml) | | standard 6 (50 mIU/ml) | | standard 7 (100 mIU/ml) | | standard 8 (200 mIU/ml) | |
|---|---|---|---|---|---|---|---|---|---|---|---|---|---|---|---|---|
| | obs | norm | obs | norm | obs | norm | obs | norm | obs | norm | obs | norm | obs | norm | obs | norm |
| 15 | 0.015 | | 0.022 | | 0.032 | | 0.108 | | 0.242 | | 0.448 | | 0.780 | | 1.250 | |

TABLE 2-continued

Results obtained by varying the volume of substrate incubation time in the LH assay (obs = observed results; norm = corrected values of LH concentration after applying the internal normalisation procedure).

| Substrate Incubation Time (Min) | standard 1 (0 mIU/ml) | | standard 2 (1 mIU/ml) | | standard 3 (2 mIU/ml) | | standard 4 (10 mIU/ml) | | standard 5 (25 mIU/ml) | | standard 6 (50 mIU/ml) | | standard 7 (100 mIU/ml) | | standard 8 (200 mIU/ml) | |
|---|---|---|---|---|---|---|---|---|---|---|---|---|---|---|---|---|
| | obs | norm | obs | norm | obs | norm | obs | norm | obs | norm | obs | norm | obs | norm | obs | norm |
| 10 | 0.012 | 0.017 | 0.016 | 0.024 | 0.022 | 0.033 | 0.073 | 0.110 | 0.171 | 0.259 | 0.317 | 0.480 | 0.577 | 0.875 | 0.925 | 1.403 |
| 20 | 0.022 | 0.016 | 0.030 | 0.023 | 0.039 | 0.029 | 0.128 | 0.096 | 0.289 | 0.217 | 0.531 | 0.399 | 0.983 | 0.738 | 1.537 | 1.157 |

TABLE 3

Results obtained by varying the volume of substrate present in the T4 assay (obs = observed results; norm = corrected values of T4 concentration after applying the internal normalisation procedure).

| Substrate Volume (μl) | standard 1 (0 ng T4) | | standard 2 (25.6 ng T4/ml) | | standard 3 (51.1 ng T4/ml) | | standard 4 (117 ng T4/ml) | | standard 5 (163 ng T4/ml) | | standard 6 (215 ng T4/ml) | | standard 7 (311 ng T4/ml) | |
|---|---|---|---|---|---|---|---|---|---|---|---|---|---|---|
| | obs | norm | obs | norm | obs | norm | obs | norm | obs | norm | obs | norm | obs | norm |
| 300 | 1.031 | | 0.952 | | 0.906 | | 0.769 | | 0.678 | | 0.568 | | 0.396 | |
| 250 | 0.864 | 0.936 | 0.809 | 0.877 | 0.777 | 0.842 | 0.630 | 0.683 | 0.561 | 0.608 | 0.464 | 0.503 | 0.332 | 0.360 |
| 350 | 0.869 | 0.942 | 0.844 | 0.915 | 0.792 | 0.859 | 0.685 | 0.743 | 0.592 | 0.642 | 0.511 | 0.554 | 0.363 | 0.393 |

TABLE 4

Results obtained by varying the substrate incubation time in the T4 assay (obs = observed results; norm = corrected values of T4 concentration after applying the internal normalisation procedure).

| Substrate Incubation Time (Min) | standard 1 (0 ng T4) | | standard 2 (2.5 ng T4/ml) | | standard 3 (51.1 ng T4/ml) | | standard 4 (117 ng T4/ml) | | standard 5 (163 ng T4/ml) | | standard 6 (215 ng T4/ml) | | standard 7 (311 ng T4/ml) | |
|---|---|---|---|---|---|---|---|---|---|---|---|---|---|---|
| | obs | norm | obs | norm | obs | norm | obs | norm | obs | norm | obs | norm | obs | norm |
| 60 | 1.031 | | 0.952 | | 0.906 | | 0.769 | | 0.678 | | 0.568 | | 0.396 | |
| 45 | 0.636 | 0.936 | 0.584 | 0.859 | 0.551 | 0.811 | 0.476 | 0.700 | 0.416 | 0.612 | 0.347 | 0.510 | 0.251 | 0.369 |
| 55 | 0.792 | 0.925 | 0.752 | 0.879 | 0.695 | 0.812 | 0.590 | 0.689 | 0.528 | 0.617 | 0.441 | 0.515 | 0.320 | 0.374 |

We claim:

1. A method of performing an immunoassay of a ligand in a liquid sample wherein two independently measureable enzyme labels are separately conjugated to two or more components or populations of components of the assay system and, after completion of the complexing reaction, substantially all of the first enzyme label and a proportion of the second enzyme label are removed from the assay mixture, the proportion of the second label removed being related to the amount of the said ligand and the assay determined from a measurement of said proportion of the second label being normalised by comparison with a measurement of the total first label removed.

2. A method of performing a 1-site immunoassay as claimed in claim 1 which includes the steps of
   (a) incubating the sample sequentially or simultaneously with a ligand analogue labelled with a first enzyme label and with an antibody to the ligand labelled with a second enzyme label (such that the said first enzyme label may be monitored independently of the said second enzyme label) to achieve complexing;
   (b) separating the complexed components containing the said first enzyme label from the fraction of said second enzyme label uncomplexed with ligand analogue; and
   (c) determining a normalised assay of the ligand by measuring the amount of the said second enzyme label in the separated complexed components from step (b) containing said first enzyme label with respect to a measurement of the said first enzyme label present in the said separated components.

3. A method as claimed in claim 2 wherein the ligand analogue labelled with the first enzyme label is also tagged with a reagent X (the said reagent not being present as a free reagent in the assay mixture) and step (b) is accomplished by means of a solid phase carrying a binding partner specific for reagent X.

4. A method of performing a 2-site immunoassay as claimed in claim 1 which includes the steps of
   (a) incubating the sample in the presence of a reagent comprising two or more populations of antibodies to the ligand which can complex simultaneously with the ligand (the reagent employing two enzyme labels such that a first label in one of the populations may be monitored independently of a second label in the other population(s)), to achieve complexing equilibrium;
   (b) separating the components containing said first enzyme label from those containing uncomplexed said second enzyme label; and
   (c) determining a normalised assay of the ligand by measuring the amount of the said second enzyme label in the separated complexed components from step (b) containing said first enzyme label with respect to a measurement of the said first label present in the said separated components.

5. A method as claimed in claim 4 which comprises incubating a mixture of
   (a) the liquid sample;
   (b) a reagent comprising antibodies to the ligand labelled with a first enzyme label;
   (c) a reagent comprising antibodies to the ligand labelled with a second independently measureable enzyme label; and (d) a reagent capable of binding to component (b) by non-covalent bonding, but which is not directly bindable to either component (a) or component (c), the said reagent (d) being bound to a solid phase support;

separating the solid phase from the assay mixture and determining a normalised assay of the ligand by measuring the amount of the said second enzyme label in the separated solid phase components with respect to a measurement of the said first label present in the said separated components.

6. A method as claimed in claim 5 wherein reagent (b) comprises antibodies conjugated to a reagent X in addition to the first enzyme label and reagent (d) is a specific binding partner for reagent X (the said reagent not being present as a free reagent in the assay mixture).

7. A method as claimed in claim 3 or claim 6 wherein reagent X is a hapten selected from fluorescein derivatives, rhodamine isothiocyanate, 2,4-dinitrofluorobenzene, phenyl isothiocyanate and danzyl chloride.

8. A method as claimed in claim 1 wherein the enzyme-substrate pairs employed are alkaline phosphatase/phenolphthalein monophosphate and $\beta$-galactosidase/p-nitrophenyl-$\beta$-D-galactoside or $\beta$-galactosidase/o-nitrophenyl-$\beta$-D-galactoside.

9. A method as claimed in claim 8 wherein the amounts of the two enzyme labels in the solid phase after separation from the assay mixture are determined by incubating the said solid phase in the presence of a substrate buffer solution at pH 8.6 initially comprising about 0.25 M to 1 M diethanolamine, about 10 mM phenolphthalein monophosphate and about 50 mM p-nitrophenyl-$\beta$-D-galactoside.

10. A kit of reagents for carrying out a method of immunoassay which comprises, in at least one container, (i) a ligand analog labelled with a first enzyme label and (ii) a reagent comprising antibodies to the ligand under assay labelled with a second enzyme label, said second enzyme being different from said first enzyme and being measurable independently of said first enzyme label.

11. A kit as claimed in claim 10 wherein said ligand analog labelled with a first enzyme label is immobilized on a solid phase.

12. A kit as claimed in claim 10 wherein the ligand analog labelled with the first enzyme label is also tagged with a reagent X and further comprising a container containing a solid phase carrying a binding partner specific for reagent X.

13. A kit of reagents for carrying out a method of immunoassay comprising in at least one container (i) a first population of antibodies to the ligand under assay labelled with a first enzyme label, and (ii) a second population of antibodies to the ligand under assay labelled with a second enzyme label, said second enzyme being different from said first enzyme and being measurable independently of said first enzyme label, said first and second population of antibodies being directed against two different epitopes.

14. A kit as claimed in claim 13 wherein said first and second populations of antibodies are in separate containers.

15. A kit as claimed in claim 13 wherein said population of antibodies labelled with a first enzyme label is immobilized on a solid phase.

16. A kit as claimed in claim 13 wherein the population of antibodies labelled with the first enzyme label is also tagged with a reagent X and further comprising a container containing a solid phase carrying a binding partner specific for reagent X.

17. A kit as claimed in claim 13 wherein said enzymes are alkaline phosphatase and $\beta$-galactosidase.

* * * * *